United States Patent [19]

Shah et al.

[11] Patent Number: 5,184,628
[45] Date of Patent: Feb. 9, 1993

[54] GRIP SINCERITY ASSESSMENT SYSTEM AND METHOD

[76] Inventors: Khalid M. Shah, Block 1C, Gilman Heights, Apt. 12-24, Singapore 0104, Singapore; James C. Semple, 59 Hamilton Dr., Glasgow G12, Scotland

[21] Appl. No.: 681,145

[22] Filed: Apr. 5, 1991

[30] Foreign Application Priority Data

Apr. 6, 1990 [GB] United Kingdom ............... 9007903

[51] Int. Cl.⁵ ............................................. A61B 5/103
[52] U.S. Cl. .................................. 128/774; 73/379.02
[58] Field of Search ............ 128/774, 779, 782; 73/379, 380, 381

[56] References Cited

U.S. PATENT DOCUMENTS

| | | | |
|---|---|---|---|
| 4,231,255 | 11/1980 | Haski et al. | 73/379 |
| 4,337,780 | 7/1982 | Metrick | 128/774 |
| 4,774,966 | 10/1988 | Lemmen | 128/774 |
| 4,885,687 | 12/1989 | Casey | 364/413.02 |
| 4,949,729 | 9/1990 | Haski | 128/774 |
| 5,050,618 | 9/1991 | Larsen | 128/774 |

Primary Examiner—Max Hindenburg
Assistant Examiner—Guy V. Tucker
Attorney, Agent, or Firm—Ratner & Prestia

[57] ABSTRACT

The sincerity or genuineness of grip exerted by a subject in orthopaedic testing is assessed by deriving a signal representing grip force over a period of about ten seconds, and comparing the rate and uniformity at which the force is applied and thereafter decays with fatigue against predetermined parameters.

8 Claims, 4 Drawing Sheets

GRIP SINCERITY ASSESSMENT SYSTEM AND METHOD

FIELD OF INVENTION

This invention relates to a system and method for assessing hand grip. More particularly, the invention relates to the assessment of the sincerity or genuineness of the grip exerted by a subject requested to grip as firmly as possible.

BACKGROUND TO INVENTION

It is known in orthopaedics to measure the mobility and the grip strength of the hand as a means of assessing injury or disease and recovery from them. One example of this is in assessing stiffness of the hand following fracture of the metacarpal bones. Measurement of the absolute value of grip strength gives a reasonable assessment of the progress of recovery; known grip meters used for this purpose are marketed by MIE Medical Research and Jamar Inc.

This method of assessment is, however, dependent on the subject making a genuine effort to exert maximum grip during the test. It is believed that some subjects deliberately attempt to conceal the degree of recovery by applying less than maximum grip. This may happen for example where there are considerations of insurance claims or industrial injury compensation.

It has previously been proposed to assess grip sincerity from force measurement; see 1. "Simple method to determine sincerity of effort during a maximal isometric test of grip strength", J. C. Gilbert et al., *Amer. J. of Physical Medicine,* 1983, pp 135-143.

2. "Assessing sincerity of effort in maximal grip strength tests", G. A. Smith et al., *Amer. J. of Physical Medicine and Rehabilitation,* 1989, pp 73-80.

It is believed, however, that these prior proposals do not provide results useful in practical evaluation. One reason is that they base the evaluation on a comparison of peak strength to average strength, which is not a reliable indicator. Another is that they assume a genuine grip to have a substantially constant force over a period of some seconds, whereas in fact the strength of a genuine grip decays relatively quickly over timescales of even a few seconds due to fatigue.

BRIEF SUMMARY OF THE INVENTION

An object of the present invention is therefore to provide improved assessment of the sincerity of the grip exerted by a subject.

Accordingly, the invention from one aspect provides a method of assessing the sincerity of a subject's grip, comprising the steps of: causing the subject to apply and hold a grip, measuring the force produced by said grip as a function of time deriving from said force measurement a force-vs-time characteristic having a load slope, followed by a fatigue slope, and comparing the parameters of force-vs-time characteristic representative of the slope thereof with like parameters of predetermined characteristics to derive a measure of deviation indicative of sincerity.

From another aspect the invention provides a grip sincerity assessment system comprising grip transducer means operable to provide a signal representative of the grip exerted thereon by a subject over a period of time, means for deriving from said signal a force-vs-time characteristic having a load slope followed by a fatigue slope, and means for comparing parameters of said characteristic with predetermined characteristics to derive a measure of deviation indicative of sincerity.

Preferably, said signal is converted to digital form before deriving the parameters. The system, apart from the grip transducer means and analog-to-digital conversion means, may most readily be embodied in a suitably programmed digital computer, but discrete special-purpose circuits could equally be used. The system may have other components to form a package capable of making a number of biomechanical measurements used in orthopaedic surgery.

The comparison may be effected by examining a ratio of two parameters of said characteristic. Preferably, said parameters are two or more of:

L = load slope (i.e. the speed at which force is applied)
F = fatigue slope (i.e. the rate at which the force declines)
M = the maximum force applied
W = the total work done in a given time
V = the variance of the applied force during the fatigue slope.

Preferably, said ratio is selected from L/M, W/L and M/V, or the log transformations of these. Most preferably, the assessment is made for more than one ratio.

BRIEF DESCRIPTION OF THE DRAWINGS

An embodiment of the invention will now be described, by way of example, with reference to the drawings, in which.

DESCRIPTION OF PREFERRED EMBODIMENTS

Figure 1:
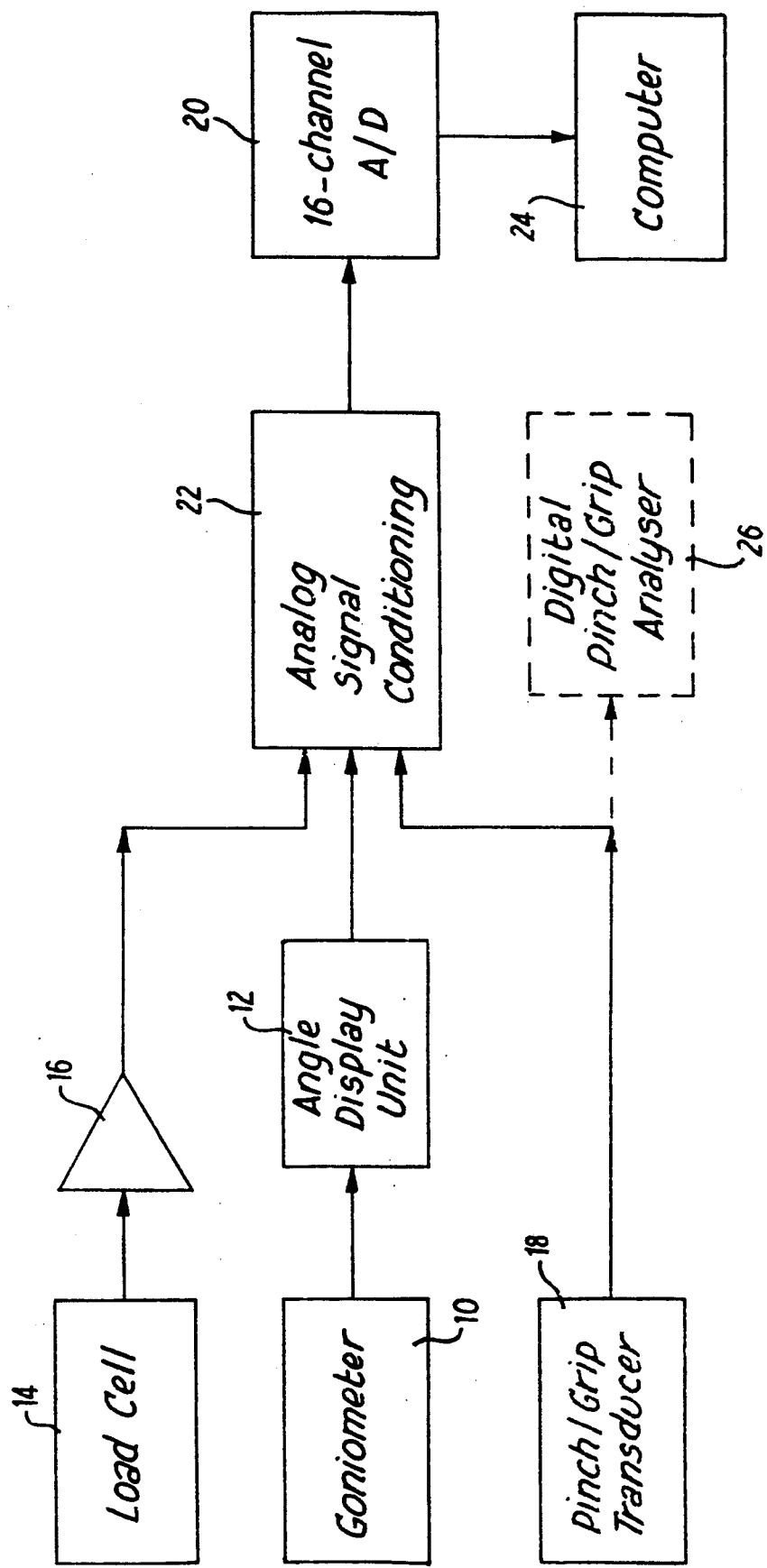
FIG. 1 is a block diagram of a system embodying the invention.

Referring to FIG. 1, the system shown is for assessing not only grip but also mobility and fracture stiffness. Mobility and fracture stiffness are assessed in known manner by means of a goniometer 10 and angle display unit 12, and a load cell 14 via a load cell amplifier 16. Grip is assessed using a known pinch/grip transducer 18 to give an analog output which is a function of the force applied by a gripping action of the subject's hand.

The analog signals from these three sensing channels are supplied to a 16-channel analog-to-digital converter 20, optionally via an analog signal conditioning module 22 for providing scaling, limiting or filtering of the analog signals in known manner. The three sensing channel signals in digitised form are supplied by the A-D converter 20 to a computer 24 which may suitably be any PC-compatible microcomputer. The analog signal from the pinch/grip transducer 18 may additionally be supplied to a digital pinch/grip analyzer 26 of known type such as that supplied by MIE Medical Research or that produced by Jamar.

The present invention makes use of the computer 24 to analyse the digitised grip information on the basis which will now be discussed.

Figure 2:
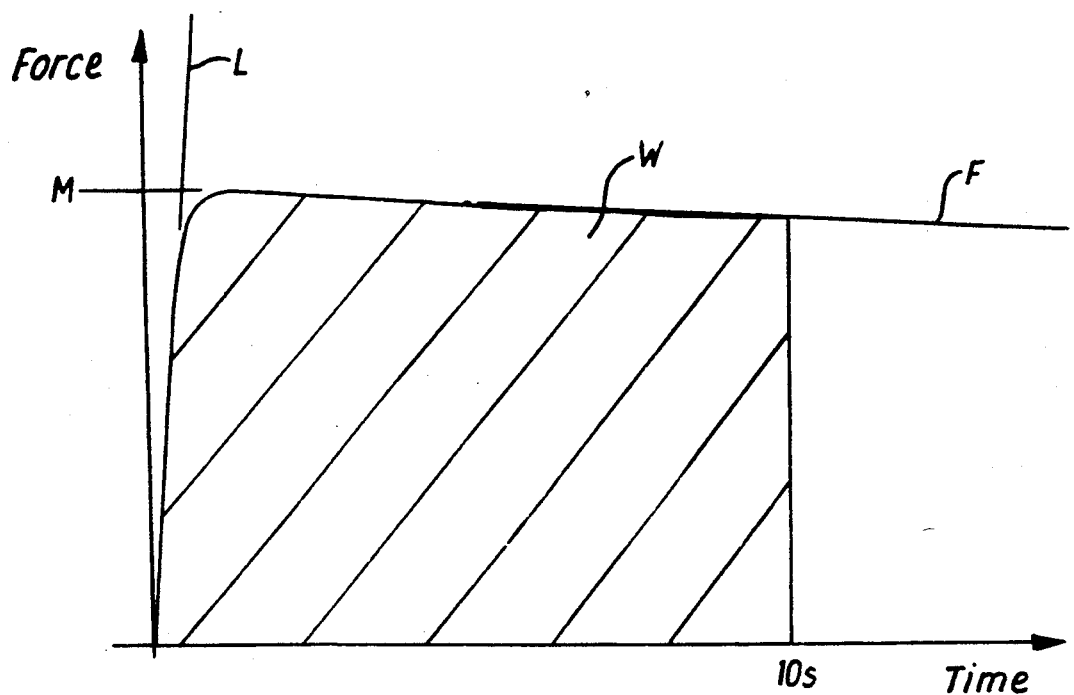
FIG. 2 is a graph of force against time illustrating the principal parameters of a hand grip.

FIG. 2 shows an idealized graph of grip force against time. The subject is asked to apply maximum grip on the transducer and maintain that grip over a test period, typically 10 s. The measured force increases fairly rapidly until a maximum force M is reached. Thereafter, the measured force declines slowly as the muscles fatigue. One may therefore define a load slope L as the best-fit slope of the first part, and a fatigue slope F as the best-fit slope of the second part. The work done W during the test is the area under the curve. A further parameter of interest is the variance V of the fatigue slope F.

We have determined that the signals obtained from sincere subjects closely follow the pattern of FIG. 2 while those of insincere subjects do not, and that these can be distinguished by examination of parameters selected from M, F, L, W and V.

Figure 3:
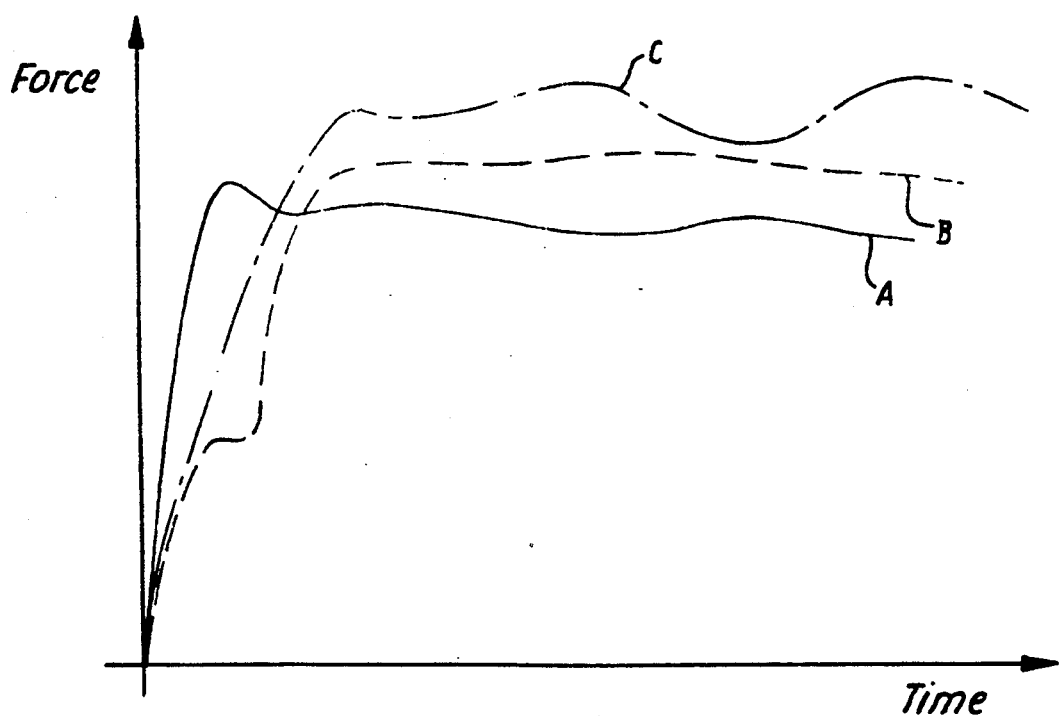
FIG. 3 is a similar graph showing typical sincere and insincere patterns.

Referring to FIG. 3, curve A shows a typical response from a sincere subject, approximating in shape to the curve of FIG. 2. Curve B shows a response from a insincere subject, in which the load slope L is interrupted, while in the insincere response of curve C there is considerable fluctuation in the fatigue zone. It will be noted that the maximum amplitude M is of no significance alone. It is the shape of the curve which is of significance; the parameters L, F, M, W and V and their various ratios define this shape.

The response can be classified as sincere or insincere by measuring selected ones of the parameters L, F, M, W and V and evaluating one or more selected functions of these. We have established the functions $L/M$ $W/L$ $M/V$ as being useful measures of sincerity. In some cases for statistical reasons transformations of these ratios may be required, for example log transformations such as log L/log M.

Figure 4:
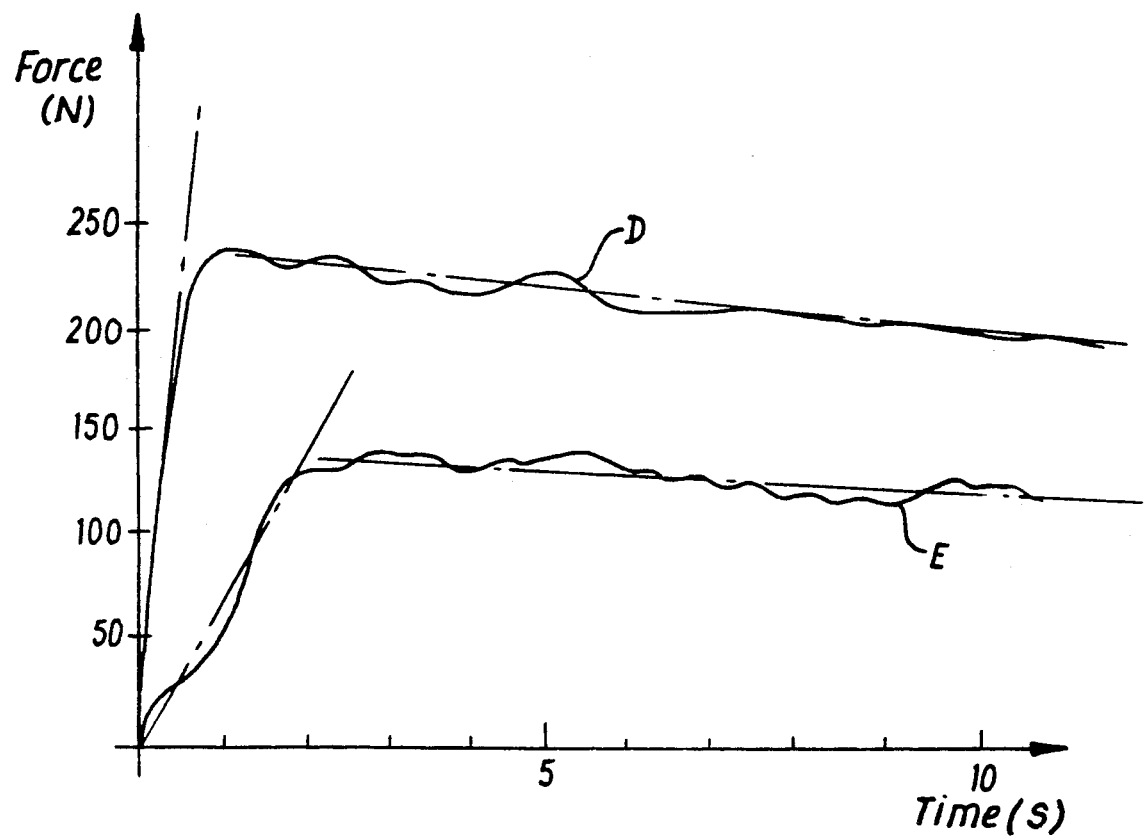
FIG. 4 is a similar graph showing sincere grips for normal and injured hands.

A frequency distribution for the selected ratio is established using a group of volunteers. Frequency distributions of these ratios due to known pathological conditions are also established in a similar way. By way of example in FIG. 4 curve D is from a normal hand and curve E from an injured hand, both grips being sincere. Any subsequent result not falling within such frequency ratio is taken to be a submaximal (fake) grip. Double blind tests of this system have given over 95% confidence limits.

The following Tables give experimental results from a group of female volunteers aged 20–40 operating with sincerity.

TABLE 1

Power grip, both hands. All values log transformed. Sample size 38.

|  | Range | Mean | S.D. |
|---|---|---|---|
| Load slope (L) | 4.87–7.00 | 5.936 | 0.533 |
| Fatigue slope (F) | 0.00–2.98 | 1.486 | 0.747 |
| Maximum (M) | 4.88–5.89 | 5.389 | 0.253 |
| Work (W) | 6.85–8.11 | 7.479 | 0.314 |
| W/M | 1.35–1.43 | 1.388 | 0.020 |
| L/M | 0.93–1.27 | 1.101 | 0.086 |
| W/L | 1.07–1.47 | 1.267 | 0.102 |
| W/F | −3.80–12.59 | 4.396 | 4.099 |
| L/F | −3.16–10.20 | 3.523 | 3.341 |
| L × M × F/W | −0.30–13.09 | 6.388 | 3.345 |

TABLE 1-continued

Power grip, both hands. All values log transformed. Sample size 38.

|  | Range | Mean | S.D. |
|---|---|---|---|
| L × M/W | 3.48–5.08 | 4.279 | 0.403 |
| L × M/F | −16.84–55.04 | 19.10 | 17.97 |
| L − F/W | 0.36–0.83 | 0.594 | 0.116 |

TABLE 2

Power grip. Non-dominant hand. Sample size 19.

|  | Range | Mean | S.D. |
|---|---|---|---|
| Load slope (L) | 4.71–6.89 | 5.799 | 0.545 |
| Fatigue slope (F) | −0.13–3.03 | 1.946 | 0.790 |
| Maximum (M) | 4.90–5.80 | 5.351 | 0.225 |
| Work (W) | 6.85–8.01 | 7.427 | 0.292 |
| W/M | 1.35–1.43 | 1.388 | 0.022 |
| L/M | 0.90–1.27 | 1.083 | 0.092 |
| W/L | 1.06–1.52 | 1.290 | 0.119 |
| W/F | −1.68–10.66 | 4.490 | 3.089 |
| L/F | −1.64–8.71 | 3.532 | 2.587 |
| L × M × F/W | −0.72–12.76 | 6.025 | 3.370 |
| L × M/W | 3.36–5.00 | 4.179 | 0.409 |
| L × M/F | −8.66–46.46 | 18.90 | 13.78 |
| L − F/W | 0.31–0.85 | 0.585 | 0.133 |

TABLE 3

Power grip. Dominant hand. Sample size 19.

|  | Range | Mean | S.D. |
|---|---|---|---|
| Load slope (L) | 5.08–7.06 | 6.073 | 0.496 |
| Fatigue slope (F) | 0.09–2.97 | 1.526 | 0.721 |
| Maximum (M) | 4.87–5.98 | 5.427 | 0.279 |
| Work (W) | 6.86–8.20 | 7.529 | 0.335 |
| W/M | 1.36–1.42 | 1.387 | 0.017 |
| L/M | 0.96–1.27 | 1.119 | 0.078 |
| W/L | 1.08–1.41 | 1.245 | 0.085 |
| W/F | −5.70–14.30 | 4.300 | 5.00 |
| L/F | −4.55–11.58 | 3.513 | 4.032 |
| L × M × F/W | 0.01–13.49 | 6.751 | 3.370 |
| L × M/W | 3.62–5.14 | 4.378 | 0.380 |
| L × M/F | −24.21–62.83 | 19.31 | 21.76 |
| L − F/W | 0.40–0.80 | 0.603 | 0.099 |

Analysis of experimental data such as the above suggests another group of ratios which could be useful in identifying complex cases. These ratios are:

W/F

L/F

L×M×F/W

L×M/W

L×M/F

L−M/W

L−F/W

The analysis of other forms of hand grip such as "key grip" (force between thumb and side of finger) and "pinch grip" (force between tip of thumb and tip of finger), which are routinely tested while examining hands, could also be carried out in the above manner and the ratios obtained could be used in conjunction with power grip parameters in assessing genuineness.

As an alternative to the use of parameter ratios as discussed above, the invention also contemplates the examination of variance of the load and fatigue slopes from a linear form. It is believed that this may most usefully be carried out on the fatigue slope.

Figure 5:
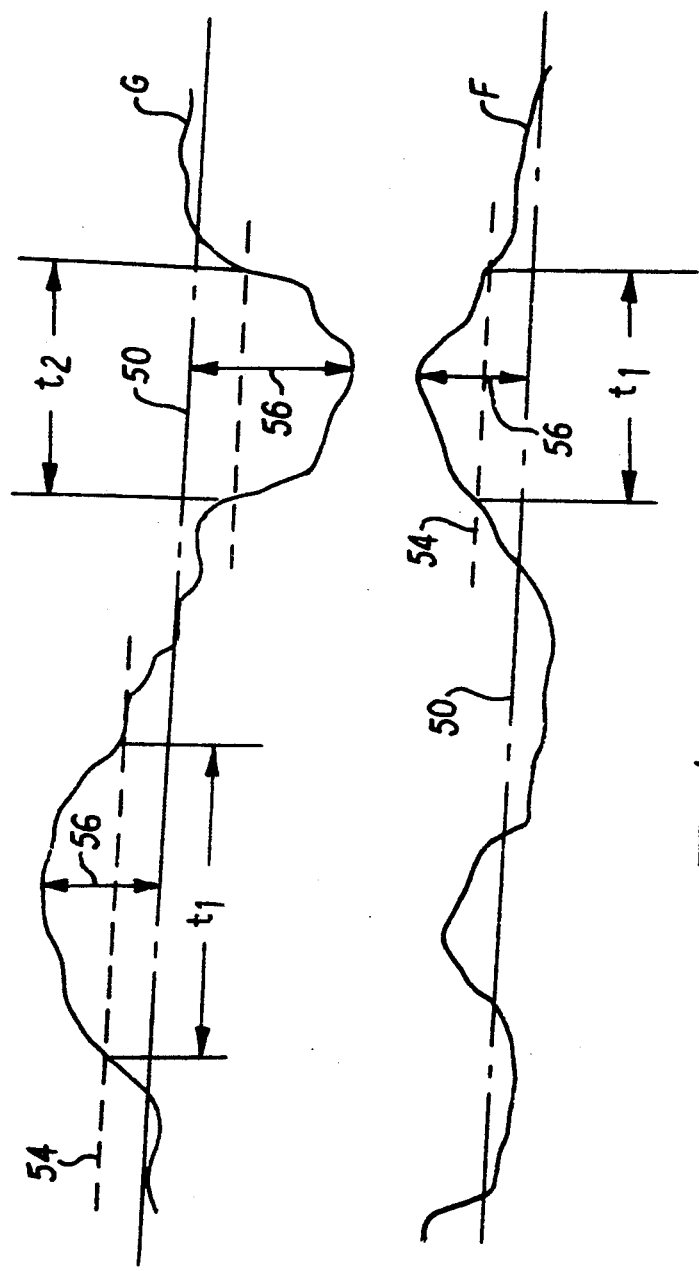
FIG. 5 is a similar graph illustrating an alternative basis for evaluating the force signal.

Referring to FIG. 5, curves F and G represent the fatigue slopes of sincere and submaximal grips, respectively, with the vertical dimension exaggerated. The evaluation can be carried out by examination of variation from a best-fit straight line 50 in a number of ways, for example:

(a) the number N of excursions 52 from the line 50 which exceed a predetermined value 54.

(b) the total time $t = t_1 + t_2 \ldots$ of such excursions 52.

(c) the maximum value 56 of any such excursion.

This can readily be accomplished on digitized signals by straightforward computational methods. Suitable values for N, t, 54 and 56 can be derived empirically from testing a cohort of subjects.

It is possible to test both hands at the same time by duplicating elements of the system. Routine testing could also take into account "cross-over testing" in which maximal effort is exerted by both hands simultaneously with the arms crossed. This form of testing after establishment of the parameters would help in further distinguishing genuine from fake grips.

The calibration of the sensor, the digitisation of the force signal, and the derivation of the foregoing parameters, ratios and variances can readily be accomplished by known techniques and therefore will not be described in detail. Although a digital general-purpose computer is preferred for processing the sensor signals, the same procedures may equally be carried out by special-purpose circuitry.

Modifications and improvements may be made without departing from the scope of the invention.

We claim:

1. A method of assessing the sincerity of a subject's grip, comprising the steps of: causing the subject to apply and hold a grip, measuring the force produced by said grip as a function of time, deriving from said force measurement a force-vs-time characteristic having a load slope followed by a fatigue slope, and comparing parameters of the force-vs-time characteristic representative of the shape thereof with like parameters of predetermined characteristics to derive a measure of deviation indicative of sincerity.

2. The method of claim 1, in which the grip is held and the force measured for about ten seconds.

3. The method of claim 1, in which said comparison comprises comparing the value of at least one of the load slope and the fatigue slope with a predetermined slope value.

4. The method of claim 1, in which said comparison comprises evaluating the deviation from a linear form of at least one of the load slope and the fatigue slope.

5. A grip sincerity assessment system comprising grip transducer means operable to provide a signal representative of the grip exerted thereon by a subject over a period of time, means for deriving from said signal a force-vs-time characteristic having a load slope followed by a fatigue slope, and means for comparing parameters of said characteristic to derive a measure of deviation indicative of sincerity, in which the comparing means operates to compare the values of one or both of the ratios L/M and W/L with prestored like parameters of predetermined characteristics, where L=load slope, M=maximum force applied, and W=the total work done in a given time.

6. The system of claim 5, including means for converting said signal to digital form, and in which the deriving and comparing means are digital.

7. The system of claim 6, in which the deriving and comparing means are provided by a digital computer.

8. The system of claim 5, in which the comparing means operates to compare with stored values the value of the ratio M/V, where M=the maximum force applied and V=the variance of the applied force during the load slope.

* * * * *